United States Patent

Ault, Jr.

[11] Patent Number: 5,808,090
[45] Date of Patent: Sep. 15, 1998

[54] PROCESS FOR PREVENTING PRECIPITATION IN CIMETIDINE INJECTION SOLUTIONS

[75] Inventor: Joseph Murray Ault, Jr., Wilmington, Del.

[73] Assignee: Endo Pharmaceuticals Inc., Chadds Ford, Pa.

[21] Appl. No.: 801,221

[22] Filed: Feb. 19, 1997

Related U.S. Application Data

[60] Provisional application No. 60/012,103, Feb. 22, 1996.

[51] Int. Cl.$^6$ ...................... C07D 233/66; C07D 233/90; A61K 31/415
[52] U.S. Cl. .................................. 548/336.5; 514/400
[58] Field of Search ........................ 548/336.5; 514/400

[56] References Cited

U.S. PATENT DOCUMENTS

| | | | |
|---|---|---|---|
| 4,024,271 | 5/1977 | Durant et al. | 424/274 |
| 4,098,898 | 7/1978 | Durant et al. | 514/400 |
| 4,220,653 | 9/1980 | Vivino | 514/400 |
| 4,537,900 | 8/1985 | Kreidl et al. | 514/400 |
| 4,749,790 | 6/1988 | Palomo-Coll et al. | 544/320 |
| 4,786,735 | 11/1988 | Graboyes et al. | 548/336.5 |
| 4,973,703 | 11/1990 | Imuta et al. | 548/336.5 |
| 5,229,137 | 7/1993 | Wolfe | 424/687 |
| 5,597,844 | 1/1997 | Chauhan et al. | 514/400 |
| 5,622,709 | 4/1997 | Szyczak | 424/423 |

FOREIGN PATENT DOCUMENTS

| | | | |
|---|---|---|---|
| 0081859 | 6/1983 | European Pat. Off. | 514/400 |
| 2386525 | 12/1978 | France | 514/400 |
| 56-104868 | 8/1981 | Japan | 514/400 |
| 56-164122 | 12/1981 | Japan | 514/400 |
| 57-54115 | 3/1982 | Japan | 514/400 |
| 57-56465 | 4/1982 | Japan | 514/400 |
| 57-120572 | 7/1982 | Japan | 514/400 |
| 57-212167 | 12/1982 | Japan | 514/400 |
| 59-130272 | 7/1984 | Japan | 548/336.5 |
| 2025969 | 1/1980 | United Kingdom | 514/400 |
| 83/00692 | of 0000 | WIPO | 514/400 |

*Primary Examiner*—Floyd D. Higel
*Attorney, Agent, or Firm*—Michael B. Fein; James A. Drobile

[57] ABSTRACT

A process for preventing precipitation of cimetidine from cimetidine injectables which involves thermally treating the cimetidine injectables, which are substantially free of precipitate, is described.

25 Claims, No Drawings

PROCESS FOR PREVENTING PRECIPITATION IN CIMETIDINE INJECTION SOLUTIONS

This application claims the benefit of U.S. Provisional Application No. 60/012,103, filed Feb. 22, 1996.

FIELD OF THE INVENTION

The present invention relates generally to a process for preventing precipitation of cimetidine from cimetidine injectables which involves thermally treating cimetidine injectables.

BACKGROUND OF THE INVENTION

Cimetidine is a histamine H2-receptor antagonist used for the treatment of duodenal and gastric ulcers, and hypersecretory conditions. Commercial preparations of cimetidine include tablet, liquid, and injectable forms as well as pre-mixed solutions for intravenous administration, see for example, Tagamet brand of cimetidine hydrochloride for injection package insert, SmithKline Beecham Pharmaceuticals, Phila., Pa. 1994 and Cimetidine Hydrochloride Injection package insert, Endo Laboratories, L.L.C., Wilmington, Del. 1994.

Since cimetidine is slightly soluble in water, formulations for intravenous injection use the more soluble hydrochloride salt of cimetidine. The concentration of cimetidine hydrochloride in commercial intravenous preparations exceeds the reported equilibrium solubility for cimetidine hydrochloride (160 mg/mL at 25° C.). Formulation above the solubility limit results in the formation of a supersaturated solution of cimetidine hydrochloride. Specifically, an aqueous solution that is formulated to contain 150 mg/mL cimetidine base, has an equivalent cimetidine hydrochloride concentration of 171.2 mg/mL. Commercial formulations of cimetidine for injection also contain 5 mg/mL of phenol and optionally sodium hydroxide or hydrochloric acid used for pH adjustment.

When cimetidine for injection is exposed to cold temperatures or stored at controlled room temperature (15°–30° C.) precipitation may occur, L. A. Trissel, ASHP Handbook on Injectable Drugs, 5th ed. American Society of Hospital Pharmacists, 1988; pg. 184. There is usually a direct relationship between temperature and solubility. If the temperature of a solution is decreased, drug solubility is decreased, and precipitation can occur. For cimetidine, temperature is a factor that has been manipulated to induce crystallization in supersaturated solutions, see B. Hedegus and S. Gorog, J. Pharm. Biomed. Anal. (1985) 3(4) pp. 303–313. Thus, precipitation of cimetidine hydrochloride is expected considering cimetidine for injection is formulated as a supersaturated solution.

Exposure of vials or ampoules to subambient temperatures can occur during manufacture, distribution, or storage of the product. Manufacture during winter months, transport in unheated vehicles or cargo holds, storage near air conditioning vents, or storage in drafty environments are examples of situations that can predispose formulations of cimetidine for injection to precipitation.

Particulate matter in parenteral fluids is a serious problem that can have fatal results. Intravenous infusion of precipitated material poses a serious medical risk to patients. Complications arising from the administration of precipitated material include pulmonary infarctions, phlebitis, thrombosis or other unexpected adverse reactions. Additionally, use of a precipitated dosage form with a corresponding decrease in potency has the potential to expose patients to sub-therapeutic doses of cimetidine. The potential hazards presented by intravenous administration of precipitated material or dosing inaccuracy has resulted in the inclusion of the following warning in the package insert for commercial formulations of cimetidine for injection, "All parenteral drug products should be inspected visually for particulate matter and discoloration prior to administration."

It is well known in the art that a variety of drugs should not be refrigerated as they are susceptible to precipitation, see J. A. Romankiewicz, J. McManus, V. P. Gotz, and H. S. Carlin, Am. J. Hosp. Pharm 1979, 36, 1541–1545. Even with warning labels, it is improbable that a drug being shipped can avoid being exposed to subambient temperatures (e.g., air conditioning) or even lengthy storage at ambient temperatures.

Goldstein, in WO 85/03202, describes a method of terminally sterilizing isotonic drug compositions which may contain cimetidine. The process requires the presence of an isotonic agent which is glycerol or optionally sorbitol or mannitol. Present cimetidine injectables, as described in the Physician's Desk Reference (PDR) 1994, do not contain glycerol, sorbitol, or mannitol. Thus, the terminal sterilization method of Hunter is not related to cimetidine injectables presently approved by the FDA.

Thus, it would be beneficial to develop a method of reducing or even eliminating cimetidine's tendency in cimetidine injectables to precipitate when exposed to ambient or subambient temperatures.

SUMMARY OF THE INVENTION

Accordingly, one object of the present invention is to reduce the susceptibility of cimetidine injectables, which are substantially free of precipitate, to precipitation at ambient and subambient temperatures.

It is another object of the present invention to provide novel thermally treated solutions of cimetidine hydrochloride which are more resistant to cimetidine precipitation than untreated cimetidine hydrochloride injection solutions.

These and other objects, which will become apparent during the following detailed description, have been achieved by the inventor's discovery that thermal treatment of cimetidine injectables, which are substantially free of precipitate, retards, compared to untreated injectables, or prevents precipitation of cimetidine hydrochloride at ambient or even subambient temperatures.

DETAILED DESCRIPTION OF THE INVENTION

Thus, in a first embodiment, the present invention provides a process for reducing the susceptibility of cimetidine injectables to precipitation, comprising:

(a) thermally treating a cimetidine injectable at a temperature and length of time sufficient to reduce precipitation susceptibility, wherein the cimetidine injectable is substantially free of precipitate.

In a preferred embodiment, the thermal treatment is performed at a temperature of from 35° C. to about 121° C.

In a more preferred embodiment, the temperature is from about 35° C. to about 85° C.

In another more preferred embodiment, the temperature is from about 35° C. to about 65° C.

In another more preferred embodiment, the temperature is from about 65° C. to about 85° C.

In a most preferred embodiment, the temperature is about 85° C.

In another most preferred embodiment, the temperature is about 65° C.

In another most preferred embodiment, the temperature is about 45° C.

In another most preferred embodiment, the temperature is about 35° C.

In another preferred embodiment, the thermal treatment is performed from about 1 minute to about 30 minutes.

In another more preferred embodiment, the thermal treatment is performed from about 5 to about 25 minutes.

In another even more preferred embodiment, the thermal treatment is performed for about 5 minutes.

In another even more preferred embodiment, the thermal treatment is performed for about 10 minutes.

In another even more preferred embodiment, the thermal treatment is performed for about 15 minutes.

In another preferred embodiment, the cimetidine injectable comprises:

(a) aqueous cimetidine hydrochloride solution; and, (b) phenol.

In a second embodiment, the present invention provides a cimetidine injectable formed by the process, comprising:

(a) thermally treating a cimetidine injectable at a temperature and length of time sufficient to reduce precipitation susceptibility, wherein the cimetidine injectable is substantially free of precipitate.

In a preferred embodiment, the thermal treatment is performed at a temperature of from 35° C. to about 121° C.

In a more preferred embodiment, the temperature is from about 35° C. to about 85° C.

In another more preferred embodiment, the temperature is from about 35° C. to about 65° C.

In another more preferred embodiment, the temperature is from about 65° C. to about 85° C.

In a most preferred embodiment, the temperature is about 85° C.

In another most preferred embodiment, the temperature is about 65° C.

In another most preferred embodiment, the temperature is about 45° C.

In another most preferred embodiment, the temperature is about 35° C.

In another preferred embodiment, the thermal treatment is performed from about 1 minute to about 30 minutes.

In another more preferred embodiment, the thermal treatment is performed from about 5 to about 25 minutes.

In another even more preferred embodiment, the thermal treatment is performed for about 5 minutes.

In another even more preferred embodiment, the thermal treatment is performed for about 10 minutes.

In another even more preferred embodiment, the thermal treatment is performed for about 15 minutes.

Cimetidine, as used herein, refers to both the free base as well as the hydrochloride salt found in cimetidine injectables, i.e., cimetidine hydrochloride. Both of these names may be used throughout the present text and are intended to encompass both forms. Cimetidine hydrochloride is usually the form used for cimetidine injectables.

The temperature of the thermal treatment sufficient to reduce precipitation susceptibility should be at least 35° C.

Preferably, the following temperatures (in °C.) are used in the present invention to reduce precipitation susceptibility of cimetidine injectables: 35, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 and above. The temperature used is dependent upon the heating equipment available, how long the storage time will be and at what temperature the injectable will or may be stored.

The duration of thermal treatment sufficient to reduce precipitation susceptibility can be anywhere from about 1 minute to about 1 hour. It is preferred to limit the duration in order to limit possible degradation of cimetidine. Therefore, a preferred duration is from about 1 minute to about 30 minutes, with from about 5 to about 25 minutes being more preferred. About 1, 2, 3, 4, 5, 6, 7, 8, 9, 10, 11, 12, 13, 14, 15, 16, 17, 18, 19, 20, 21, 22, 23, 24, and 25 minutes can be effective at reducing precipitation susceptibility.

Cimetidine injectables are well known to those of skill in the art. Cimetidine injectables, as used herein, are cimetidine injection solutions used to administer, via injection, cimetidine to a patient. Cimetidine injectables, as used herein, are meant to cover any cimetidine injection solution (e.g., intravenous) which is susceptible to precipitation. As cimetidine has a very low solubility in water, cimetidine hydrochloride is used in cimetidine injectables. According to the Physician's Desk Reference (PDR) 1994, cimetidine to be used for injection has a concentration of 300 mg/2 mL. Thus, cimetidine injectables, as used herein, correspond to cimetidine injection solutions prepared by FDA approved methods and contain FDA approved concentrations of cimetidine (i.e., 300 mg/2 mL). Therefore, standard cimetidine injection solutions are actually supersaturated solutions from which cimetidine, in the form of cimetidine hydrochloride, readily precipitates. Reduction of precipitation susceptibility, as used herein, means that the baseline susceptibility of cimetidine injectables after thermal treatment according to the present invention has been lowered compared with cimetidine injectables which have not been treated according to the present invention.

Injectables "substantially free of precipitate," as used herein, are injectables which preferably do not contain a precipitate visible to the naked eye or contain a small enough amount that one of ordinary skill in the art would not consider the need to redissolve the precipitate before administering the injectable or discarding the injectable outright. One of ordinary skill in the art would realize that a cimetidine injectable which is substantially free of precipitate could be a freshly prepared injectable or one that has not been subjected to conditions which cause precipitation, e.g., subambient temperatures.

Cimetidine precipitate, as used herein, is intended to include all forms of precipitates (e.g., powders and flocculants). In addition, cimetidine crystallization from cimetidine injectables is also included. One of ordinary skill in the art would recognize precipitated cimetidine can be seen by visual inspection of the cimetidine injectable.

Thermal treatment, according to the present invention, involves heating a cimetidine injectable which is otherwise ready for injection into a patient, i.e., substantially free of precipitate. Cimetidine injectables are often placed into single and multi-dose vials, both of which can be treated according to the present invention. In addition, the present invention contemplates treating cimetidine injectables in any vessel containing them.

Heat can be applied to a cimetidine injectable in a variety of ways. For example, vials containing cimetidine injectables could be (a) placed in a water bath, (b) autoclaved, (c) treated with steam, (d) placed in an oven, or (e) microwaved. The preceding list is not meant to be inclusive, as one of ordinary skill in the art would readily understand that a variety of heating techniques could be used.

The ability of the container/closure system to withstand thermal treatment should be considered when selecting an appropriate means of heating. Additionally, dimensions and composition of the container and solution volume should be considered when selecting a method and duration of thermal treatment. One of ordinary skill in the art would readily understand the limits of the container containing a cimetidine injectable and could easily choose a safe and effective means of heating the injectable.

Preferably, the present thermal treatment process is performed on cimetidine injectables which are absent or at least substantially free of glycerol, mannitol and sorbitol. Substantially free, as used herein, preferably means less than 0.5 wt % based on the weight of the injectable, more preferably less than 0.1 wt %, even more preferably less than 0.01 wt %, and most preferably less than 0.001 wt %.

Other features of the invention will become apparent in the course of the following descriptions of exemplary embodiments which are given for illustration of the invention and are not intended to be limiting thereof.

EXAMPLES

Formation of cimetidine injectables is well known to one of skill in the art. As noted above, according to the Physician's Desk Reference (PDR) 1994, cimetidine to be used for injection has a concentration of 300 mg/2 mL. One of ordinary skill in the art would readily be able to form such a solution. In addition, cimetidine injectables are readily available for purchase.

Solutions of cimetidine for injection can be prepared by dissolving cimetidine hydrochloride in a sufficient volume of sterile water for injection, USP, to make a final concentration of 150 mg/mL. Containers composed of plastic, glass or stainless steel may be used for compounding cimetidine for injection. The solution may be heated and/or stirred to aid dissolution of cimetidine hydrochloride. A quantity of phenol is usually added to produce a final concentration of 5 mg/mL phenol in the cimetidine for injection solution. The pH of the solution may be adjusted to between 3.6 and 6.0 using hydrochloric acid, or sodium hydroxide, if necessary. The solutions may be filtered using a variety of pharmaceutically acceptable materials (e.g., nylon or Teflon) with a range of pore sizes applicable to aseptic filtration (i.e., 0.2 $\mu$m or less). Containers are then filled with an appropriate volume of solution, stoppered (if applicable), sealed, and labeled.

In the following examples, vials were thermally treated by immersion in a circulating water bath at the corresponding time and temperature. Vials at 121° C. (autoclaved) were autoclaved for the appropriate cycle time. Following thermal treatment vials were visually inspected and placed in a cardboard box for storage. Vials stored at 4° and 25° C. were placed in constant temperature chambers while vials stored at 15° C. were placed in a lyophilization chamber. Prior to inspection, vials were removed from the chamber and allowed to come to ambient temperature. Examination for precipitate consisted of visual observation in a light box according to USP XXIII. Following examination, vials were returned to the appropriate chambers. For the following examples, all tests for all time points and conditions were performed in a similar manner.

EXAMPLE 1

Effect of thermal treatment at 45, 65, 85, and 121° C. on the precipitation of cimetidine for injection stored at 4 and 25° C.

| Thermal Treatment | Non-precipitated vials at day: | | | | | | Day precipitate first observed |
|---|---|---|---|---|---|---|---|
| (time (min.)) | 2 | 7 | 14 | 28 | 63 | 170 | |
| 4° C. Storage | | | | | | | |
| 25° C. (Control) | 2/15 | 0/15 | 0/15 | 0/15 | 0/15 | 0/15 | 2[a] |
| 45° C. (15) | 15/15 | 12/15 | 9/15 | 3/15 | 0/15 | 0/15 | 4 |
| 65° C. (15) | 15/15 | 14/15 | 10/15 | 10/15 | 7/15 | 7/15 | 7 |
| 85° C. (15) | 15/15 | 15/15 | 14/15 | 12/15 | 6/15 | 6/15 | 14 |
| 121° C.[b] (1) | 15/15 | 15/15 | 15/15 | 15/15 | 15/15 | 15/15 | NA |
| 25° C. Storage | | | | | | | |
| 25° C. (Control) | 12/15 | 12/15 | 12/15 | 12/15 | 12/15 | 11/15 | 2[a] |
| 45° C. (15) | 15/15 | 15/15 | 15/15 | 15/15 | 15/15 | 15/15 | NA |
| 65° C. (15) | 15/15 | 15/15 | 15/15 | 15/15 | 15/15 | 15/15 | NA |
| 85° C. (15) | 15/15 | 15/15 | 15/15 | 15/15 | 15/15 | 15/15 | NA |
| 121° C.[b] (1) | 15/15 | 15/15 | 15/15 | 15/15 | 15/15 | 15/15 | NA |

[a]No visual inspection was performed on day 1.
[b]Autoclaved.

For vials stored at 25° C. (ambient temperature) thermal treatment completely reduced precipitation susceptibility compared with untreated vials; 4 untreated vials precipitated versus none of the thermally treated vials. At the 4° C. storage condition, thermal treatment delayed the onset of precipitation for all tested temperatures.

EXAMPLE 2

Effect of varying the temperature (45, 50, 55, 60 and 65° C.) and duration (5, 10, and 15 minutes) of thermal treatment on the precipitation of cimetidine for injection stored at 4 and 25° C.

| | Non-precipitated vials at day: | | | | | | |
|---|---|---|---|---|---|---|---|
| Thermal Treatment | 1 | 6 | 14 | 27 | 41 | 77 | 122 |
| 4° C. Storage | | | | | | | |
| 25° C. (Control) | 0/5 | 0/5 | 0/5 | 0/5 | 0/5 | 0/5 | 0/5 |
| 45° C. (15 minutes) | 5/5 | 5/5 | 4/5 | 1/5 | 1/5 | 0/5 | 0/5 |
| 50° C. (15 minutes) | 5/5 | 4/5 | 2/5 | 2/5 | 0/5 | 0/5 | 0/5 |
| 55° C. (5 minutes) | 5/5 | 5/5 | 5/5 | 1/5 | 0/5 | 0/5 | 0/5 |
| 55° C. (10 minutes) | 5/5 | 4/5 | 2/5 | 1/5 | 0/5 | 0/5 | 0/5 |
| 55° C. (15 minutes) | 5/5 | 5/5 | 2/5 | 2/5 | 2/5 | 0/5 | 0/5 |
| 60° C. (5 minutes) | 5/5 | 5/5 | 2/5 | 1/5 | 1/5 | 0/5 | 0/5 |
| 60° C. (10 minutes) | 5/5 | 5/5 | 4/5 | 0/5 | 0/5 | 0/5 | 0/5 |
| 60° C. (15 minutes) | 5/5 | 4/5 | 2/5 | 1/5 | 0/5 | 0/5 | 0/5 |
| 65° C. (5 minutes) | 5/5 | 4/5 | 4/5 | 2/5 | 1/5 | 0/5 | 0/5 |
| 65° C. (10 minutes) | 5/5 | 5/5 | 4/5 | 2/5 | 1/5 | 0/5 | 0/5 |
| 65° C. (15 minutes) | 5/5 | 4/5 | 2/5 | 2/5 | 0/5 | 0/5 | 0/5 |
| 25° C. Storage | | | | | | | |
| 25° C. (Control) | 5/5 | 3/5 | 3/5 | 3/5 | 3/5 | 3/5 | 3/5 |
| 45° C. (15 minutes) | 5/5 | 5/5 | 5/5 | 5/5 | 5/5 | 5/5 | 5/5 |
| 50° C. (15 minutes) | 5/5 | 5/5 | 5/5 | 5/5 | 5/5 | 5/5 | 5/5 |
| 55° C. (5 minutes) | 5/5 | 5/5 | 5/5 | 5/5 | 5/5 | 5/5 | 5/5 |
| 55° C. (10 minutes) | 5/5 | 5/5 | 5/5 | 5/5 | 5/5 | 5/5 | 5/5 |
| 55° C. (15 minutes) | 5/5 | 5/5 | 5/5 | 5/5 | 5/5 | 5/5 | 5/5 |
| 60° C. (5 minutes) | 5/5 | 5/5 | 5/5 | 5/5 | 5/5 | 5/5 | 5/5 |
| 60° C. (10 minutes) | 5/5 | 5/5 | 5/5 | 5/5 | 5/5 | 5/5 | 5/5 |
| 60° C. (15 minutes) | 5/5 | 5/5 | 5/5 | 5/5 | 5/5 | 5/5 | 5/5 |
| 65° C. (5 minutes) | 5/5 | 5/5 | 5/5 | 5/5 | 5/5 | 5/5 | 5/5 |

-continued

| Thermal Treatment | Non-precipitated vials at day: | | | | | | |
|---|---|---|---|---|---|---|---|
| | 1 | 6 | 14 | 27 | 41 | 77 | 122 |
| 65° C. (10 minutes) | 5/5 | 5/5 | 5/5 | 5/5 | 5/5 | 5/5 | 5/5 |
| 65° C. (15 minutes) | 5/5 | 5/5 | 5/5 | 5/5 | 5/5 | 5/5 | 5/5 |

As observed in Example 1, thermal treatment according to the present invention was effective at preventing precipitation in vials stored at 25° C. Thermal treatment substantially delayed precipitation in vials stored at 4° C. compared with untreated vials (control), as observed in Example 1.

EXAMPLE 3

Effect of thermal treatment on the refrigerated storage (4° C.) of cimetidine for injection.

| Thermal Treatment | Non-precipitated vials at day: | | | | | | Day precipitate first observed |
|---|---|---|---|---|---|---|---|
| | 1 | 7 | 13 | 28 | 56 | 155 | |
| 4° C. Storage | | | | | | | |
| 25° C. (Control) | 4/19 | 0/19 | 0/19 | 0/19 | 0/19 | 0/19 | 1 |
| 45° C. (15 minutes) | 20/20 | 16/20 | 8/20 | 4/20 | 1/20 | 1/20 | 3 |
| 85° C. (15 minutes) | 20/20 | 20/20 | 20/20 | 18/20 | 12/20 | 12/20 | 20 |
| 121° C.[a] (1 minute) | 20/20 | 20/20 | 20/20 | 20/20 | 20/20 | 17/17[b] | NA |

[a]Autoclaved.
[b]Three vials were dropped and broken.

Thermal treatment according to the present invention substantially delayed or prevented precipitation in vials stored at 4° C.

EXAMPLE 4

Effect of thermal treatment on storage at three temperatures, 4, 15, and 25° C.

| Thermal Treatment | Non-precipitated vials at day: | | | | | |
|---|---|---|---|---|---|---|
| | 1 | 7 | 13 | 55 | 77 | 127 |
| 4° C. Storage | | | | | | |
| 25° C. (Control) | 2/5 | 1/5 | 1/5 | 1/5 | 1/5 | 0/5 |
| 35° C. (15 minutes) | 5/5 | 5/5 | 4/5 | 4/5 | 4/5 | 4/5 |
| 40° C. (15 minutes) | 5/5 | 5/5 | 4/5 | 4/5 | 4/5 | 4/5 |
| 45° C. (15 minutes) | 5/5 | 4/5 | 4/5 | 4/5 | 4/5 | 4/5 |
| 50° C. (15 minutes) | 5/5 | 5/5 | 5/5 | 5/5 | 5/5 | 5/5 |
| 55° C. (15 minutes) | 5/5 | 5/5 | 5/5 | 5/5 | 5/5 | 4/5 |
| 60° C. (15 minutes) | 5/5 | 4/5 | 3/5 | 3/5 | 3/5 | 3/5 |
| 15° C. Storage | | | | | | |
| 25° C. (Control) | 1/5 | 1/5 | 1/5 | 0/5 | 0/5 | 0/5 |
| 35° C. (15 minutes) | 5/5 | 5/5 | 5/5 | 5/5 | 4/5 | 4/5 |
| 40° C. (15 minutes) | 5/5 | 5/5 | 5/5 | 4/5 | 4/5 | 4/5 |
| 45° C. (15 minutes) | 5/5 | 5/5 | 5/5 | 5/5 | 5/5 | 5/5 |
| 50° C. (15 minutes) | 5/5 | 5/5 | 5/5 | 5/5 | 5/5 | 5/5 |
| 55° C. (15 minutes) | 5/5 | 5/5 | 5/5 | 5/5 | 5/5 | 5/5 |
| 60° C. (15 minutes) | 5/5 | 5/5 | 5/5 | 5/5 | 5/5 | 5/5 |
| 25° C. Storage | | | | | | |
| 25° C. (Control) | 4/5 | 4/5 | 4/5 | 4/5 | 4/5 | 4/5 |
| 35° C. (15 minutes) | 5/5 | 5/5 | 5/5 | 5/5 | 5/5 | 5/5 |
| 40° C. (15 minutes) | 5/5 | 5/5 | 5/5 | 5/5 | 5/5 | 5/5 |
| 45° C. (15 minutes) | 5/5 | 5/5 | 5/5 | 5/5 | 5/5 | 5/5 |
| 50° C. (15 minutes) | 5/5 | 5/5 | 5/5 | 5/5 | 5/5 | 5/5 |
| 55° C. (15 minutes) | 5/5 | 5/5 | 5/5 | 5/5 | 5/5 | 5/5 |
| 60° C. (15 minutes) | 5/5 | 5/5 | 5/5 | 5/5 | 5/5 | 5/5 |

Thermal treatment according to the present invention is effective at reducing the susceptibility of cimetidine injectables to precipitation even at 15° C.

Examples 1–4 show that thermal treatment according to the present invention is effective at reducing the susceptibility to precipitation of cimetidine injectables stored at 25° C. and 4° C. Furthermore, thermal treatment according to the present invention of previously precipitated injectables effectively reduces reprecipitation in vials stored at 25° C. and 4° C. It is noted that it would appear the higher the thermal treatment temperature the greater the reduction in observed precipitation susceptibility.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of United States is:

1. A process for reducing the susceptibility of a cimetidine injectable to precipitation, comprising:
   (a) thermally treating a cimetidine injectable, wherein the cimetidine injectable is substantially free of precipitate, at a temperature of from 35° C. to about 121° C. and for about 1 minute to about 30 minutes.

2. A process according to claim 1, wherein the temperature is from about 35° C. to about 85° C.

3. A process according to claim 2, wherein the temperature is from about 35° C. to about 65° C.

4. A process according to claim 2, wherein the temperature is from about 65° C. to about 85° C.

5. A process according to claim 2, wherein the temperature is about 85° C.

6. A process according to claim 2, wherein the temperature is about 65° C.

7. A process according to claim 2, wherein the temperature is about 45° C.

8. A process according to claim 2, wherein the temperature is about 35° C.

9. A process according to claim 1, wherein the thermal treatment is performed from about 5 to about 25 minutes.

10. A process according to claim 9, wherein the thermal treatment is performed for about 5 minutes.

11. A process according to claim 9, wherein the thermal treatment is performed for about 10 minutes.

12. A process according to claim 9, wherein the thermal treatment is performed for about 15 minutes.

13. A process according to claim 1, wherein the cimetidine injectable, comprises:
   (a) aqueous cimetidine hydrochloride solution; and,
   (b) phenol.

14. A heat treated cimetidine injectable formed by a process, comprising:
   (a) thermally treating a cimetidine injectable, wherein the cimetidine injectable is substantially free of precipitate, at a temperature of from about 35° C. to about 121° C. and for about 1 minute to about 30 minutes.

15. A cimetidine injectable according to claim 14, wherein the temperature is from about 35° C. to about 85° C.

16. A cimetidine injectable according to claim 15, wherein the temperature is from about 35° C. to about 65° C.

17. A cimetidine injectable according to claim 15, wherein the temperature is from about 65° C. to about 85° C.

18. A cimetidine injectable according to claim 15, wherein the temperature is about 85° C.

19. A cimetidine injectable according to claim 15, wherein the temperature is about 65° C.

20. A cimetidine injectable according to claim 15, wherein the temperature is about 45° C.

21. A cimetidine injectable according to claim 15, wherein the temperature is about 35° C.

22. A cimetidine injectable according to claim 14, wherein the thermal treatment is performed from about 5 to about 25 minutes.

23. A cimetidine injectable according to claim 22, wherein the thermal treatment is performed for about 5 minutes.

24. A cimetidine injectable according to claim 22, wherein the thermal treatment is performed for about 10 minutes.

25. A cimetidine injectable according to claim 22, wherein the thermal treatment is performed for about 15 minutes.

* * * * *